(12) United States Patent
Jenny

(10) Patent No.: US 6,391,629 B1
(45) Date of Patent: May 21, 2002

(54) DEVICE FOR THE PRODUCTION OF AN ANAEROBIC, MICRO-AEROPHILIC OR ANOTHER ATMOSPHERE IN A CLOSED INTERCHANGEABLE CONTAINER

(76) Inventor: Alois Jenny, Oberdorf 2, CH-6215 Beromünster (CH)

( * ) Notice: Subject to any disclaimer, the term of this patent is extended or adjusted under 35 U.S.C. 154(b) by 0 days.

(21) Appl. No.: 09/526,494

(22) Filed: Mar. 15, 2000

(30) Foreign Application Priority Data

Mar. 16, 1999 (CH) ............................................. 0503/99

(51) Int. Cl.$^7$ ................................................ C12M 1/00
(52) U.S. Cl. ..................... 435/303.2; 141/21; 141/65; 141/66; 141/347; 141/348; 251/58
(58) Field of Search ........................... 435/303.1, 303.2; 141/4, 8, 18, 21, 65, 66, 347–350; 251/58

(56) References Cited

U.S. PATENT DOCUMENTS

| | | | | |
|---|---|---|---|---|
| 4,188,265 A | * | 2/1980 | Larro ......................... | 435/313 |
| 5,454,421 A | * | 10/1995 | Kerger et al. .................. | 141/18 |
| 5,588,970 A | * | 12/1996 | Hughett et al. ............. | 29/623.2 |
| 6,063,619 A | * | 5/2000 | Tachi et al. .............. | 435/303.2 |
| 6,265,210 B1 | * | 7/2001 | Silley et al. ............. | 435/303.1 |

* cited by examiner

*Primary Examiner*—David A. Redding
(74) *Attorney, Agent, or Firm*—Wenderoth, Lind & Ponack, L.L.P.

(57) ABSTRACT

The invention relates to a static unit (1) for the production of anaerobic, micro-aerophilic or other atmospheres (e.g., CO2) in a mobile interchangeable container, which is connected, at a lid of the unit to the system for the production of the desired atmosphere in the interior of the interchangeable container. The invention also relates to an interchangeable container particularly suitable for such a device. The static unit (1) can receive mobile interchangeable containers in an aperture provided for this purpose, in which the desired atmosphere in the interior is produced fully automatically. A vacuum-operated docking cylinder automatically couples the interchangeable container, which has an internal gas supply channel for the system (4) for the production of the desired atmosphere and is pressed gastight against an area of the interchangeable container lid having gas inlets and outlets.

20 Claims, 4 Drawing Sheets

DEVICE FOR THE PRODUCTION OF AN ANAEROBIC, MICRO-AEROPHILIC OR ANOTHER ATMOSPHERE IN A CLOSED INTERCHANGEABLE CONTAINER

BACKGROUND OF THE INVENTION

The invention relates to a device for the production of an anaerobic, micro-aerophilic or similar type of atmosphere in a closed interchangeable container including a lid. The container can be connected to a unit to provide the desired atmosphere inside the container for the incubation of microorganisms inside the container. Such atmospheres are known to be required in microbiology, medicine, pharmacology and in research for the cultivation of anaerobic, micro-aerophilic and other micro-organisms. For this purpose, laboratory samples (on nutrient mediums in Petri dishes) are placed in the interchangeable container, which is subsequently inserted in an aperture of the unit provided. This automatically attaches the interchangeable container to the unit and establishes the desired atmosphere by program-controlled evacuation and gassing. Following the end of the program, the interchangeable container is removed from the device and placed in a warming cupboard for incubation to proceed.

In the case of the "Anoxomat" described in the prospectus "MART systems—a standard for microbiology throughout the world", a control device is described for the partial automation of the type of gassing and evacuation specified above. This control device is provided with free connecting tubes to which a vessel can be attached for the production of the anaerobic atmosphere. The corresponding connecting elements are provided as manual coupling parts on the lid of the vessel. Several cables, connecting tubes and connecting elements are provided for the control system, vacuum pump and gas cylinders, which results in a complicated handling procedure. In addition, the vacuum pump, which is not integrated in the control unit, must be set up somewhere on the outside. Thus, there is a danger of faulty operation as a result of the use of the wrong connecting tubes and/or incorrectly connecting these elements. Furthermore, the "temporary" connecting tubes and cables and/or the manually-connected elements of the vessel lid and control unit as well as the vacuum pump are exposed and, as a consequence, highly susceptible to damage.

SUMMARY OF THE INVENTION

The present invention is based on the need to eliminate these disadvantages and to create a device of the nature specified in the introduction, in which a mobile interchangeable container containing the laboratory samples can be inserted simply, rapidly and reliably in the aperture of a static unit, and a desired atmosphere can subsequently be produced in the interior of the interchangeable container without any appreciable manual labor.

The invention solves this problem by providing elements to automatically connect and disconnect a gas supply unit to an interior of an interchangeable container. The elements form an alternating system for creating the desired atmosphere inside the container by evacuating and gassing.

In one very advantageous version, a static unit is provided with an integrated vacuum pump, various gas connections, gas valves, and a vacuum-operated docking cylinder. The interchangeable container is attached, gas-tight, by the docking cylinder, and the interchangeable container is evacuated and gassed once or several times in accordance with a program until the desired atmosphere has been established in the interior of the interchangeable container.

In the device of the invention, it is only necessary to bring the interchangeable containers containing the laboratory samples into the aperture provided in the unit and then to push the start button. This is followed by fully automatic coupling, evacuation and gassing for the establishment of the desired atmosphere without any manual activity. The process reliability of the device is also guaranteed by the fact that no tubes or manual coupling elements are present and that, in the case of the docking cylinder, gas is supplied through an internal channel. There are also no protruding connecting elements on the interchangeable container. This gives rise to the advantage that the interchangeable containers can be stacked and thus stored in the warming cupboard in a manner that saves a great deal of space. Furthermore, the vacuum-operated docking cylinder facilitates a simple and space-saving method of construction of the static unit.

It is an advantage if, in accordance with the invention, the docking cylinder is formed of a cylinder piston unit, wherein a cylinder is fixed to the device and the piston has, on the side of the interchangeable container, a docking attachment that can be moved against a coaxial pressure spring. The docking cylinder is provided, at the front, with a sealing ring that can be pressed against the lid of the interchangeable container. The piston, including the piston ring and docking attachment, is fitted with an internally continuous channel for the evacuation and supply of gas. As a result of this construction, the docking cylinder requires almost no maintenance and offers process reliability.

In order to facilitate the seizure and handling of the interchangeable container, the invention provides for the interchangeable container to be made of lightweight material (polycarbonate, aluminum) and for vertical ribs to be arranged over its circumference.

In order to achieve as simple and maintenance-free closure of the interchangeable container as possible, the invention also provides for the lid of the interchangeable container to be fitted with a bayonet catch. The catch is expediently provided with a lip seal on the inner edge of the interchangeable container and has, in the middle of the closure, in the position of the docking cylinder, gas inlet and outlet channels, in which a back-pressure valve is installed in each instance.

The invention also provides for the floor of the interchangeable container to be provided with a recess at its center that corresponds with a correspondingly constructed elevation in the lid of the interchangeable container. In this way, the interchangeable containers can be centered and simply stacked on top of one another.

BRIEF DESCRIPTION OF THE DRAWINGS

Further features of the invention are shown in the subsequent description, with reference to the following drawings, including.

DETAILED DESCRIPTION OF THE INVENTION

Figure 1:
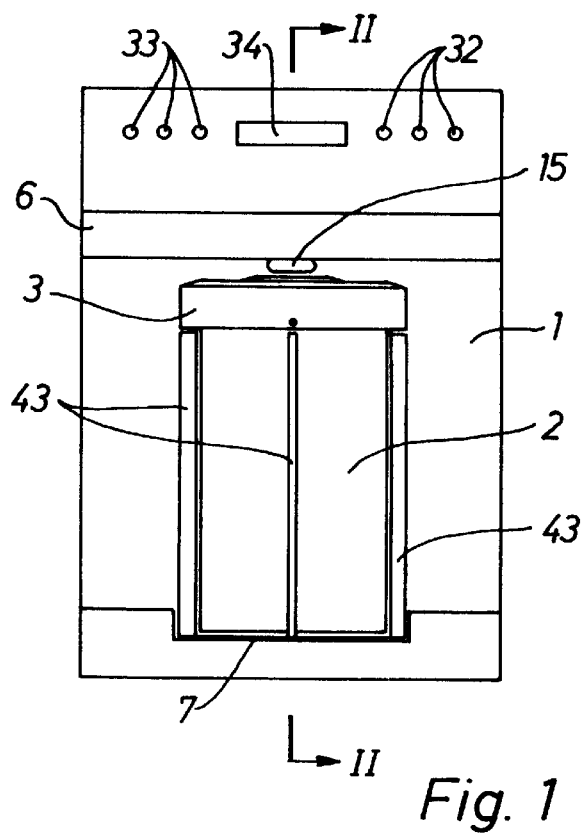
FIG. 1 is a device in accordance with the invention for the production of anaerobic, micro-aerophilic or other atmospheres in a closed interchangeable container, shown in front view.
Figure 2:
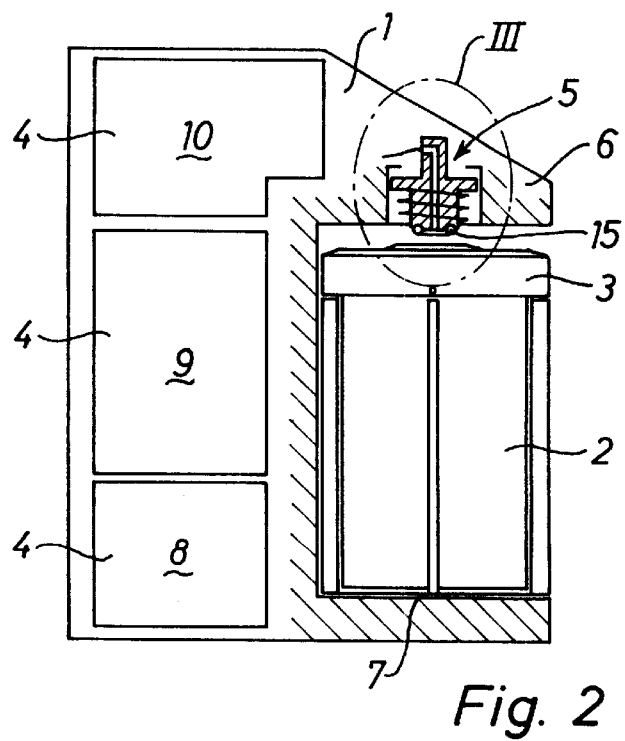
FIG. 2 is the device of FIG. 1, shown in a cross-section along the II—II line in FIG. 1.

FIGS. 1 to 5 show a static gas supply unit 1 for the production of anaerobic, micro-aerophilic or other similar atmospheres in a closed interchangeable container 2 that is provided with a lid 3. The gas supply unit 1 is equipped with a system 4 for the production of the desired atmosphere in the interior of the interchangeable container. The interchangeable container 2 can be coupled to the lid side of the system 4 by means of a vacuum-operated docking cylinder 5 that is installed in a mounting portion 6 of the unit 1. Below the mounting portion 6, an aperture 7 is located in the unit 1 for the positioning of the interchangeable container.

The system 4 is composed of three structural elements 8, 9 and 10, whereby the first structural element 8 is provided with a vacuum pump 24, and the second structural element 9 is fitted with at least one gas supply source 26a, 26b, docking cylinder 5, switching valves 29a to 29e and a vacuum sensor 31 with the corresponding sensors. Push button 32, display 33 and a printer 34 are attached to the third structural element 10, such as a control and program unit 10.

According to the invention, the static unit 1 includes elements for the automatic connecting and, respectively, detaching of the system 4 with and, respectively, from the interior of the interchangeable container. The feature makes it possible for the interchangeable containers 2 to take the form of an alternating system for creating the desired atmosphere in the interchangeable container as a result of evacuation and gassing.

A vacuum-operated docking cylinder 5 for automatically connecting or detaching the system 4 with and, respectively, from the interior of the interchangeable container 2. The vacuum-operated docking cylinder 5 is formed of a cylinder piston unit 11, 12, whereby the cylinder 11 is fixed in the mounting portion 6 of the unit 1. The piston includes, on the side nearest to the interchangeable container, a docking attachment 13 protruding from the cylinder 11 that, together with the piston ring 12, can be moved against a coaxial pressure spring 14. The docking cylinder 5 includes at the front of the piston, a sealing ring 15 which presses against the lid of the interchangeable container 3. The docking attachment 13 is supported gas-tight in a front wall 16 of the cylinder 11 at the container side (i.e., closest to the container) and the pressure spring 14 is inserted in the cylinder between the piston ring 12 and the front wall 16 of the cylinder 11.

The piston is provided on the side farthest from the interchangeable container 2 with a piston pin 18 including the gas pipe connection 17 of the docking cylinder 5, which protrudes from the open cylinder 11 at the rear side of the cylinder farthest from the container. The piston ring 12, the docking attachment 13 and the piston pin 18 are coaxially arranged and an axial gas inlet and outlet channel 19 penetrates therethrough which opens out into the gas pipe connection 17 of the high-speed coupling. Close to the front wall on the container side the cylinder 11 is a vacuum pipe connection 20. The sealing ring 15 of the docking attachment 13 is formed by an O-ring seal that is held in an annular tee-slot 21 of the docking attachment 13 and overhangs this at the front in the direction of stroke of the piston.

The cylinder 11 is fastened in the mounting portion 6 of the unit 1 with screws that can be screwed into tap-holes 22 of the cylinder 11. At the open (rear) end of the cylinder at the rear, two studs 23 are provided to limit the piston stroke.

Figure 5:
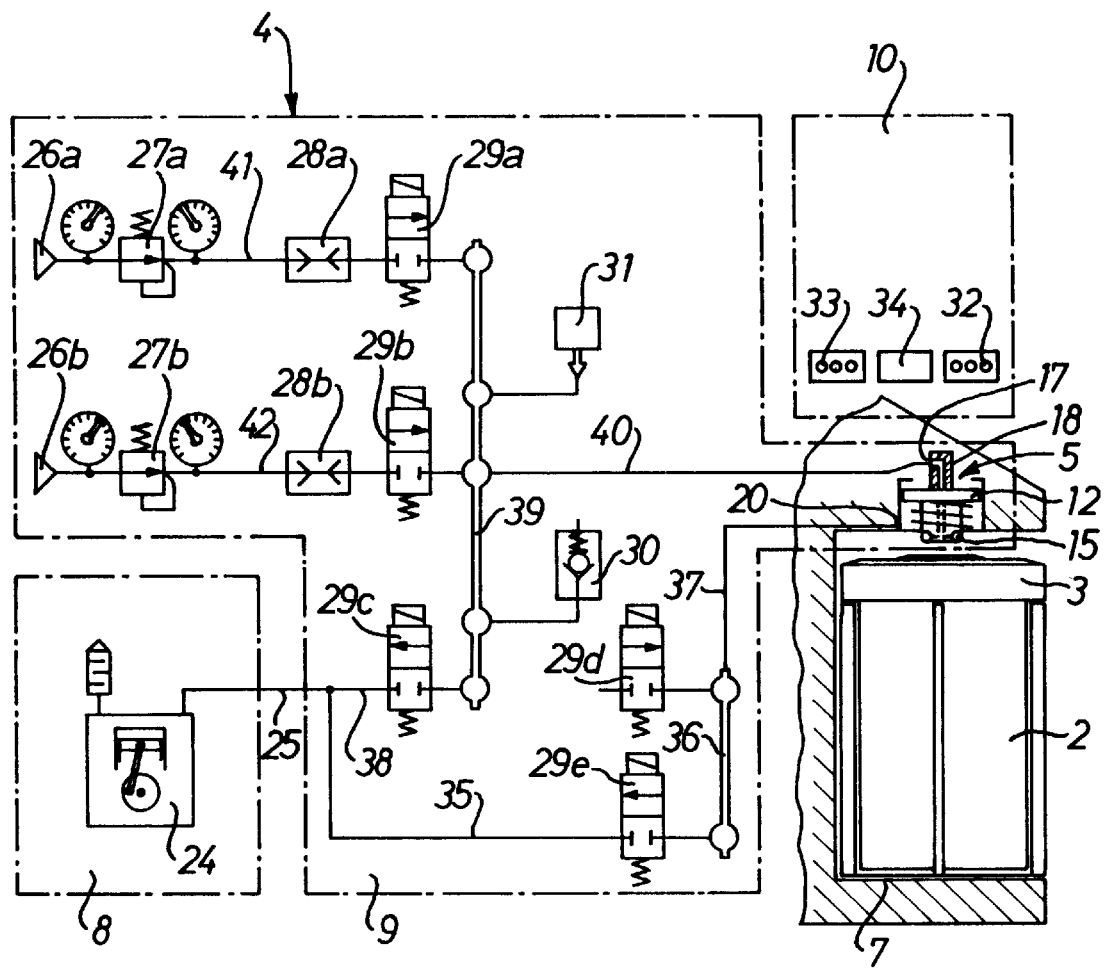
FIG. 5 is a schematic representation of the pneumatic plan for the device of FIGS. 1 to 4.

In accordance with FIG. 5, the vacuum pump 24 of the first structural element 8 is connected, by a pipe 25, to the second structural element 9. The second structural element 9 is fitted with the gas supply sources 26a and 26b, the pressure regulators 27a and 27b, the throttles 28a and 28b, the switching valves 29a to 29e formed as fork valves as well as the relief valve 30 and the vacuum sensor 31. These elements are connected to the control and programming unit (third structural element) 10 having the push buttons 32, the displays 33 and the printer 34.

The vacuum pump 24 can be connected, on the front side of the docking cylinder, to the vacuum pipe connection 20 of the cylinder 11 by the pipes 25 and 35, the switching valve 29e, a distributor 36 and a pipe 37. On the rear side of the docking cylinder, the vacuum pump can be connected to the gas pipe connection 17 of the piston pin 18 by the pipes 25 and 38, the switching valve 29c, a distributor 39 and a pipe 40. The vacuum pipe connection 20 can also be connected with the external atmosphere by the pipe 37, the distributor 36 and the switching valve 29d.

The gas supply sources 26a and 26b supply, in each instance, the desired gas or gas mixture for the production of the anaerobic atmosphere, the exact dosing of which can be exactly adjusted by means of the pressure regulators 27a and 27b as well as the throttles 28a and 28b.

In the example, source 26a supplies pure N2 and source 26b a gas mixture of N2, N2 and CO2. The component 4 can obviously also be provided with a single gas supply source or with more than two gas supply sources. In addition, a gas mixture of approximately only CO2 can be provided.

The pressure supply source 26a can be connected with the gas pipe connection 17 of the piston pin 18 by a pipe 41, the switching valve 29a, the distributor 39 and the pipe 40. Similarly, the pressure supply source 26b can also be connected with the gas pipe connection 17 of the piston pin 18 by a pipe 42, the switching valve 29b, the distributor 39 and the pipe 40. The excess pressure valve 30 and the vacuum sensor 31 are both connected to the distributor 39.

Figure 3:
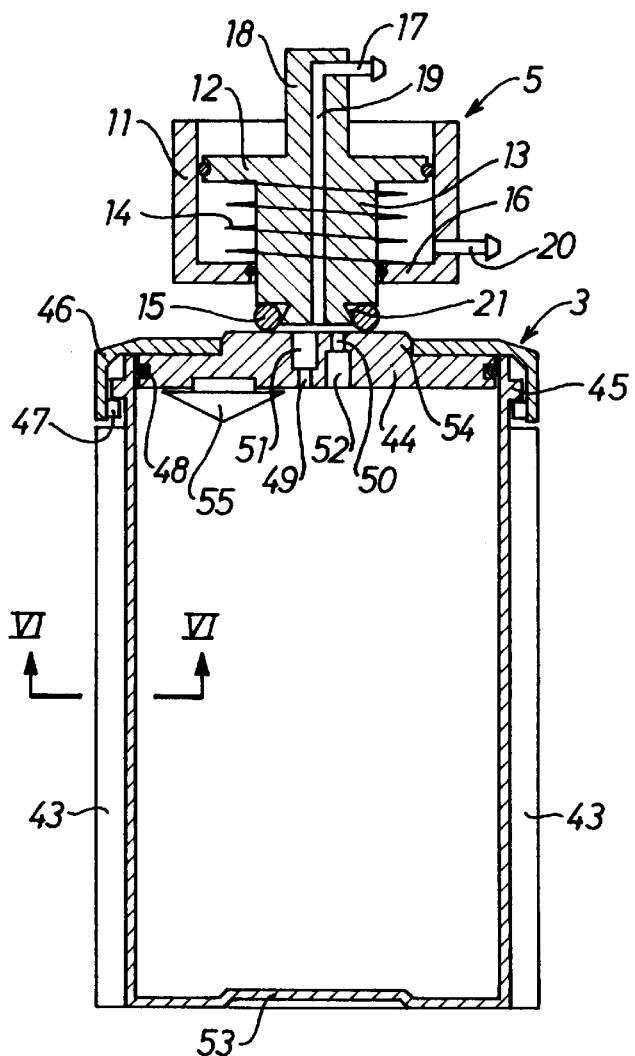
FIG. 3 is a magnification of the partial cross-section III of FIG. 2.
Figure 4:
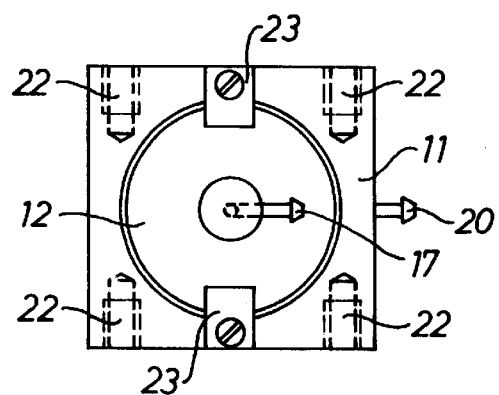
FIG. 4 shows a top view of the docking cylinder of the device of FIGS. 1 and 2.
Figure 6:
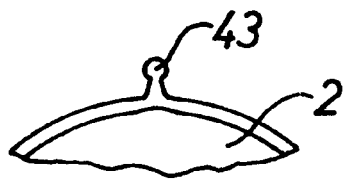
FIG. 6 is a part-section along the VI—VI line in FIG. 3.
Figure 7:
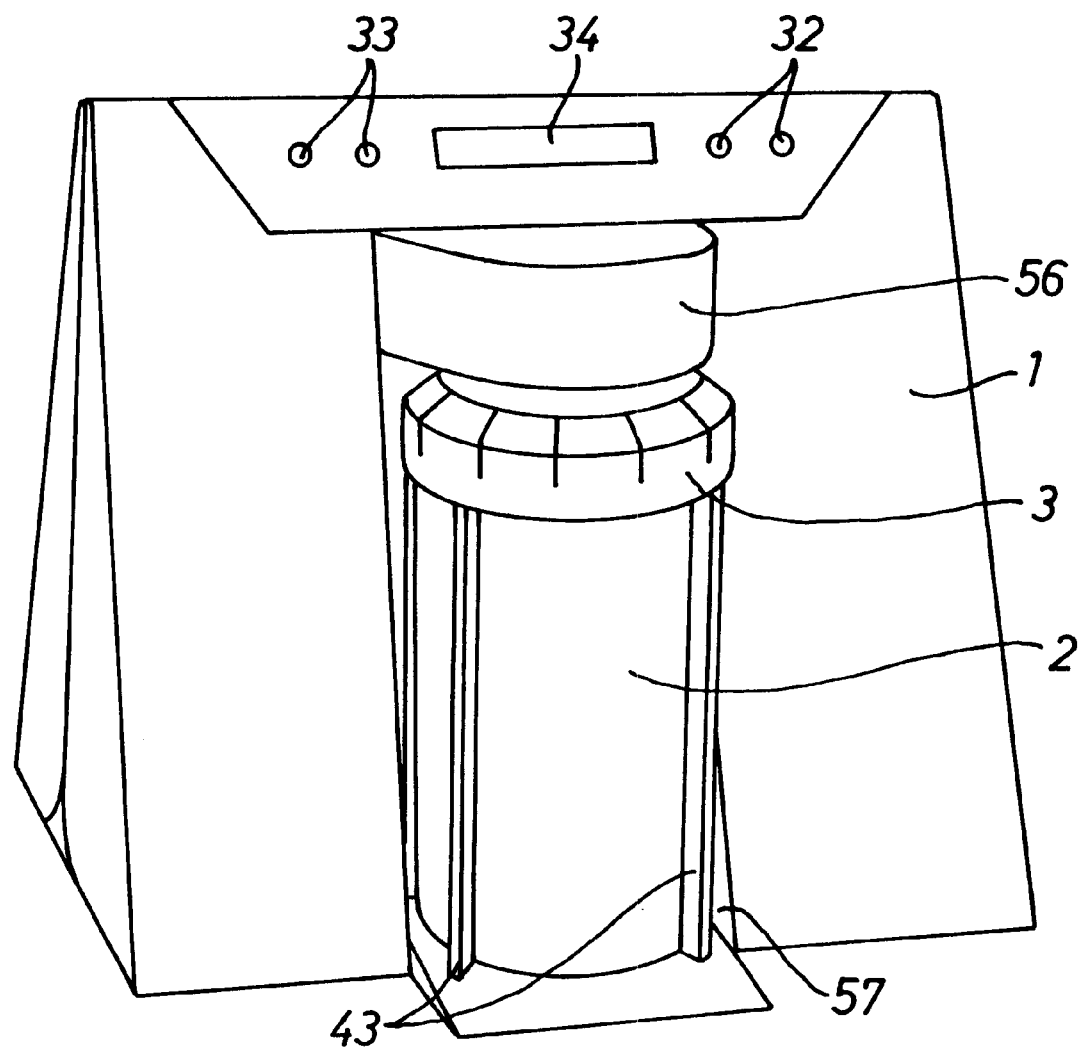
FIG. 7 is a second version of the device as a "triangular profile" with the arrangement of the internal system in the two side parts of the housing.

As shown in FIG. 7, the interchangeable container 2 for the device in accordance with the description above is formed of a pot body having vertical ribs 43 arranged over the circumferential surface. Thus, the interchangeable container can easily be handled and inserted into the aperture 7 of static unit 1. As FIG. 6 shows, the vertical ribs 43 are rounded off at their external edges. As shown in FIG. 3, the lid 3 of the interchangeable container 2 comprises a disk divider 44 having an outer circumference substantially equal to the internal circumference of the interchangeable container 2, and a fastening ring 46 embracing a circumferential rib 45 of the interchangeable container 2 by using a bayonet closure 47. The width of each of the vertical ribs 43 of the interchangeable container 2 is dimensioned so that each rib 15 flush with a fastening ring 46 over the circumference. The disk divider 44 includes a lip seal 48 over its circumference and has, in the center, gas inlet and outlet channels 49, 50, in each of which a back-pressure valve 51, 52 is fitted. The floor of the interchangeable container is provided with a recess 53 at the center which corresponds with (i.e., has the same height and diameter as) a correspondingly structured elevation (connection section) 54 of the interchangeable container lid 3. The recesses 53 and elevated connection section 54 can be enmeshed to facilitate the stacking of the interchangeable containers on top of one another. The disk divider 44 also has a catalyzer 55 that extends into the interior of the interchangeable container.

The device in accordance with FIG. 7 differs from the device of FIGS. 1 to 6 essentially only in that the side profile of unit 1 is triangular and all the internal elements are housed in the two side parts, and an aperture 57 is provided for the reception of the interchangeable container 2.

The device described above operates as follows:

Initially, the laboratory samples to be treated (Petri dishes) are place in the interchangeable container 2 that is then closed gas-tight with the lid 3 and positioned in the aperture 7 or 57, respectively, below the mounting portion 6 or 56, respectively, of the docking cylinder.

Subsequently, a push button 32 starts the program that is fully automatic. Initially, the docking cylinder 5 is activated by connecting the cylinder 11 with the vacuum pump 24 by the switching valve 29*e*. As a consequence, a vacuum is created in the cylinder 11 that causes a displacement of the piston ring 12 and the docking attachment 13 until the sealing ring 15, as is shown in FIG. 3, is pressed gas-tight against the middle area of the interchangeable container 3 with the gas inlet and outlet channels 49, 50, and this pressure is maintained by closing the switching valve 29*e*. Between the opposite sides of the piston ring 12 and the interchangeable container lid 3, a gas chamber is formed that is sealed against the external atmosphere and that is connected, on the one side, with the gas pipe connection 17 of the piston and, on the other, with the interior of the interchangeable container 2 by the gas inlet and outlet channels 49, 50. In this way the interchangeable container 2 is connected both to the vacuum pump 24 and to one of the gas supply sources 26*a*, 26*b* of the system 4.

To produce the anaerobic atmosphere, the connection to the vacuum pump 24 is initially created by the switching valve 29*c*. The interior of the interchangeable container 2 is evacuated through the gas outlet channel 50, the gas pipe channel 19 and the gas pipe connection 17. Following the attainment of the desired vacuum, measured by the vacuum sensor 31 in the interchangeable container, the connection with the vacuum pump 24 is now broken again with the switching valve 29*c* and a connection with one of the gas supply sources 26*a*, 26*b* is established by switching the valves 29*a* or 29*b*. In this manner the gas or gas mixture provided in each instance is passed to the interior of the interchangeable container 2 until the desired atmosphere has been established there. During the entire operation, the gas-tight connection of the interchangeable container 2 at the vacuum pump 24 and, respectively, with the gas supply sources 26*a*, 26*b* is secured by the vacuum-driven docking cylinder 5.

The vacuum sensor 31 and the displays 33 serve for the monitoring and display of the vacuum and/or the current condition of the process. After the desired atmosphere. has been established in the interchangeable container, the docking cylinder 5 is detached again. For this purpose the switching valve is switched on. Thus a ventilation connection is produced between the vacuum cylinder 11 and the external atmosphere.

The pressure spring 14 moves the piston ring 12 and the docking attachment 13 with the sealing ring 15 back again and the docking cylinder 5 is thus released again. Subsequently the interchangeable container 2 can be taken out of the device 1 and placed, for example, in a warming cabinet for the incubation of the samples. Then the next interchangeable container can be docked and provided with the desired atmosphere.

Obviously the elements of the invention for automatic connecting and, respectively, detachment of the system 4 with and, respectively, from the interior of the interchangeable container 2 may take a form different from the cylinder piston unit described above. For example, there may be an electromechanical solution or such like.

What is claimed is:

1. A device for producing an atmosphere in a closed container for incubation of micro-organisms, comprising:

a gas supply unit including a system for supplying gas, said system including a vacuum-operated docking cylinder, said docking cylinder including:

a cylinder having a front wall;

a piston-including a piston ring and a docking attachment connected to said piston ring and having a sealing ring at a front end thereof, said docking attachment being arranged so as to protrude from said front wall of said cylinder so as to be supported by said front wall in a gas-tight manner, said piston having an internal gas supply channel and having a gas pipe connection at a rear end of said piston for receiving gas into said gas supply channel; and a pressure spring for biasing said piston, said pressure spring being arranged between said piston ring of said piston and said front wall of said cylinder; and a container including a lid having a connection section including an inlet port and an outlet port, said container being adapted to be temporarily fitted to said gas supply unit such that said front wall of said cylinder is closer to said container than said piston ring, said piston of said docking cylinder being adapted to press said sealing ring of said docking attachment against said connection section of said lid so as to automatically removably connect said system of said gas supply unit to an interior of said container in a gas-tight manner, said system being adapted to evacuate said interior of said container and to fill said interior with gas.

2. The device of claim 1, wherein said pressure spring is arranged so as to be coaxial with said piston ring and said docking attachment.

3. The device of claim 1, wherein said piston further includes a piston pin connected to a rear side of said piston ring so as to extend away from said container, said gas pipe connection being located on said piston pin.

4. The device of claim 3, wherein said docking attachment, said piston ring, and said piston pin are coaxially arranged, said internal gas supply channel extending through said docking attachment, said piston ring, and said piston pin.

5. The device of claim 1, wherein said cylinder includes a vacuum pipe connection between said front wall of said cylinder and said piston ring of said piston.

6. A device for producing an atmosphere in a closed container for incubation of microorganisms, comprising:

a gas supply unit including a system for supplying gas, said system including a vacuum-operated docking cylinder, said docking cylinder including:

a cylinder;

a piston including a piston ring, a docking attachment connected to a front side of said piston ring and having a sealing ring at a front end thereof, and a piston pin connected to a rear side of said piston ring, said docking attachment being arranged so as to protrude from said cylinder, said piston having an internal gas supply channel and having a gas pipe connection on said piston pin for receiving gas into said gas supply channel; and a pressure spring for biasing said piston; and a container including a lid having a connection section including an inlet port and an outlet port, said container being adapted to be temporarily fitted to said gas supply unit such that said piston pin extends away from said container, said piston of said docking cylinder being adapted to press said sealing ring of said docking attachment against said connection section of said lid so as to automatically removably connect said system of said gas supply unit to an interior of said container in a gas-tight manner, said system being adapted to evacuate said interior of said container and to fill said interior with gas.

7. The device of claim 6, wherein said pressure spring is arranged so as to be coaxial with said piston ring and said docking attachment.

8. The device of claim 6, wherein said docking attachment, said piston ring, and said piston pin are coaxially arranged, said internal gas supply channel extending through said docking attachment, said piston ring, and said piston pin.

9. The device of claim 6, wherein said cylinder includes a vacuum pipe connection between said front wall of said cylinder and said piston ring of said piston.

10. A device for producing an atmosphere in a closed container for incubation of micro-organisms, comprising:

a gas supply unit having a system for supplying gas, said system including a plurality of elements, said elements comprising:
    a first structural element including a vacuum pump;
    a second structural element including a gas supply source, a docking cylinder, switching valves, and a regulator; and
    a third structural element including a push button and a display; and
a container including a lid, said elements of said system of said gas supply unit being adapted to automatically removably connect said system of said gas supply unit to said container, and said system being adapted to evacuate an interior of said container and to fill said interior with gas after being connected to said container.

11. The device of claim 10, wherein said third structural element further includes a printer.

12. The device of claim 10, wherein said docking cylinder includes:

a cylinder;
a piston including a piston ring and a docking attachment connected to said piston ring and having a sealing ring at a front end thereof, said docking attachment being arranged so as to protrude from said cylinder, said piston having an internal gas supply channel and having a gas pipe connection at a rear end of said piston for receiving gas into said gas supply channel; and
a pressure spring for biasing said piston.

13. The device of claim 12, wherein said piston of said docking cylinder is adapted to press said sealing ring of said docking attachment against said lid so as to automatically removably connect said system of said gas supply unit to an interior of said container in a gas-tight manner.

14. A device for producing an atmosphere in a closed container for incubation of micro-organisms, comprising:

a gas supply unit having a system for supplying gas, said system including a plurality of elements; and
a container including a lid having a gas inlet port including a back-pressure valve and having a gas outlet port including a back-pressure valve, said elements of said system of said gas supply unit being adapted to automatically removably connect said system of said gas supply unit to said container, and said system being adapted to evacuate an interior of said container and to fill said interior with gas after being connected to said container.

15. The device of claim 14, wherein said container is shaped as a pot having a plurality of vertical ribs arranged around a circumference of said container.

16. The device of claim 15, wherein said lid includes a disk divider having an outer circumference substantially equal to an inner circumference of a body of said container, and includes a fastening ring having a bayonet closure for embracing an edge of said body of said container.

17. The device of claim 14, wherein said plurality of elements includes a docking cylinder, said docking cylinder includes:

a cylinder;
a piston including a piston ring and a docking attachment connected to said piston ring and having a sealing ring at a front end thereof, said docking attachment being arranged so as to protrude from said cylinder, said piston having an internal gas supply channel and having a gas pipe connection at a rear end of said piston for receiving gas into said gas supply channel; and
a pressure spring for biasing said piston.

18. The device of claim 17, wherein said piston of said docking cylinder is adapted to press said sealing ring of said docking attachment against said lid so as to automatically removably connect said system of said gas supply unit to an interior of said container in a gas-tight manner.

19. A device for producing an atmosphere in a closed container for incubation of micro-organisms, comprising:

a gas supply unit having a system for supplying gas, said system including a vacuum-operated docking cylinder, said docking cylinder including:
    a cylinder having a front wall and a vacuum pipe connection; and
    a piston including a piston ring and a docking attachment coaxially connected to said piston ring and having a sealing ring at a front end thereof, said piston having an internal gas supply channel extending through said piston ring and said docking attachment, said piston being arranged in said cylinder such that said docking attachment extends through said front wall of said cylinder in a gas-tight manner, said vacuum pipe connection being located between said piston ring and said front wall of said cylinder; and
a container including a lid, said container being adapted to be temporarily fitted to said gas supply unit such that said front wall of said cylinder is closer to said container than said piston ring, said piston being adapted to press said seal ring of said docking attachment against said lid in a gas-tight manner so as to automatically removably connect said system of said gas supply unit to said container, said system being adapted to evacuate said interior of said container and to fill said interior with gas.

20. The device of claim 19, wherein said docking cylinder further includes a pressure spring arranged within said cylinder between said front wall of said cylinder and said piston ring of said piston.

* * * * *